(12) United States Patent
Fischer et al.

(10) Patent No.: US 7,418,858 B2
(45) Date of Patent: Sep. 2, 2008

(54) METHOD AND SYSTEM FOR RIPPLE-SPRING COMPRESSION ASSESSMENT

(75) Inventors: Mark William Fischer, Pittsburgh, PA (US); Hans Diebäcker, Mülheim an der Ruhr (DE); Harry L. Sill, Pittsburgh, PA (US); Philip M. Arbogast, Casa Grande, AZ (US)

(73) Assignee: Siemens Power Generation, Inc., Orlando, FL (US)

( * ) Notice: Subject to any disclaimer, the term of this patent is extended or adjusted under 35 U.S.C. 154(b) by 521 days.

(21) Appl. No.: 11/153,126

(22) Filed: Jun. 15, 2005

(65) Prior Publication Data

US 2006/0283234 A1  Dec. 21, 2006

(51) Int. Cl.
*G01L 1/04* (2006.01)
(52) U.S. Cl. .......................................... 73/161; 73/818
(58) Field of Classification Search ................... 73/820, 73/818, 161
See application file for complete search history.

(56) References Cited

U.S. PATENT DOCUMENTS

| | | | |
|---|---|---|---|
| 4,677,578 A | 6/1987 | Wright et al. | |
| 4,962,660 A | 10/1990 | Dailey et al. | |
| 5,020,234 A | 6/1991 | Alkire et al. | |
| 5,295,388 A | 3/1994 | Fischer et al. | |
| 5,325,008 A * | 6/1994 | Grant | 310/214 |
| 5,365,166 A * | 11/1994 | Dailey et al. | 324/158.1 |
| 5,557,216 A * | 9/1996 | Dailey et al. | 324/772 |
| 6,120,833 A | 9/2000 | Bonnebat et al. | |
| 6,631,335 B2 | 10/2003 | Lusted et al. | |

* cited by examiner

*Primary Examiner*—Max Noori

(57) ABSTRACT

A method and system for directly measuring the compression of a ripple spring (23) in a dynamoelectric machine through a corresponding wedge (27). A compression-assessment tool (3) is provided that includes a carriage (32) for supporting a proximity sensor (34). The carriage (32) enables the proximity sensor (34) to be passed over the length of the ripple spring (23), which produces an output signal that is representative of the compression of the ripple spring (23).

15 Claims, 3 Drawing Sheets

METHOD AND SYSTEM FOR RIPPLE-SPRING COMPRESSION ASSESSMENT

FIELD OF THE INVENTION

The present invention relates generally to the assessment of the condition of dynamoelectric machines, and more particularly to methods and systems for measuring the compression of ripple springs in dynamoelectric machines. Although the following discussion focuses on electric generators, methods and systems consistent with the present invention are applicable to other dynamoelectric machines, including electric motors.

BACKGROUND

Electric generators include a rotor and a stator. Rotors are generally constructed from a steal forging and include a number of slots that run the length of the rotor. Rotors are electrically wound by placing conductors referred to as rotor windings into the slots of the rotor.

Stators are generally constructed from a number of stacked, metal laminations. Stators also include slots, which run the length of the stator. Stators are electrically wound by placing conductors known as stator coils into the slots of the stator.

Conventional stator coils are often held in place in stator slots using a wedge and ripple spring configuration. In this configuration, a stator coil is placed into a slot, and a wedge is driven into groove near the top of the slot. A ripple spring is positioned above the stator coil and below the wedge. This ripple spring provides compressive force to keep the stator coils held firmly in the slot.

Over time, stator wedges may become loose. If a stator wedge becomes loose, it can permit a stator coil to vibrate, which can cause catastrophic failure in an electric generator. In order to avoid stator-coil vibration and catastrophic failure of a generator, it is desirable to periodically inspect the tightness of ripple springs. However, such inspections present a challenge because ripple springs are difficult to access within a generator and because they are concealed by the corresponding stator wedge.

There are a number of conventional approaches to inspecting the compression of ripple springs. One approach involves manually tapping the stator wedges. Another approach involves measuring the depth of the surface of ripple springs through pre-formed test holes in the wedge. A third approach involves physically displacing the wedge and measuring the resulting wedge movement.

There are significant challenges associated with the conventional approaches to testing ripple-spring tightness. The first approach, manually tapping stator wedges, is extremely subjective. The results vary greatly between different inspectors. Manually tapping stator wedges is also only possible after a generator's rotor has been removed from the generator.

The second approach, using a depth gauge to take measurements through pre-formed test holes, is time consuming. This approach is also only possible when a generator has pre-formed test holes in its stator wedges. Many generators do not have such pre-formed test holes.

The third approach, physically displacing the stator wedge, involves impacting a stator wedge and then measuring the displacement of the stator wedge with a sensor such as an optical or capacitive sensor to give an indirect indication of the compression of the ripple spring beneath the stator wedge. This method is not ideal because it involves only an indirect indication of ripple-spring compression. This approach also requires a relatively complex algorithm for converting the displacement of the stator wedge into an indication of ripple-spring compression. U.S. Pat. No. 5,295,388 to Fischer et al, which is incorporated by reference herein in its entirety, discloses a method and system that utilizes this approach.

Despite advances in the area of ripple-spring compression assessment, improved methods and systems are still needed to enable fast, accurate, and direct measurement of ripple-spring compression in generators that do not necessarily have pre-formed test holes.

SUMMARY OF THE INVENTION

Methods and systems consistent with the present invention enable the direct measurement of the compression of ripple springs in dynamoelectric machines, such as electric generators. A compression-assessment tool that includes a non-contact proximity sensor is passed over the length of the stator wedge. The proximity sensor provides a mapping of the compression of the ripple spring by taking direct measurements of the proximity of the ripple spring through the wedge material that lies over the ripple spring. In a preferred embodiment, methods and systems consistent with the present invention may be utilized to assess ripple-spring tightness on a generator while the generator's rotor is in situ.

BRIEF DESCRIPTION OF THE DRAWINGS

The invention is explained further by way of example with reference to the following drawings.

DETAILED DESCRIPTION

Figure 1:
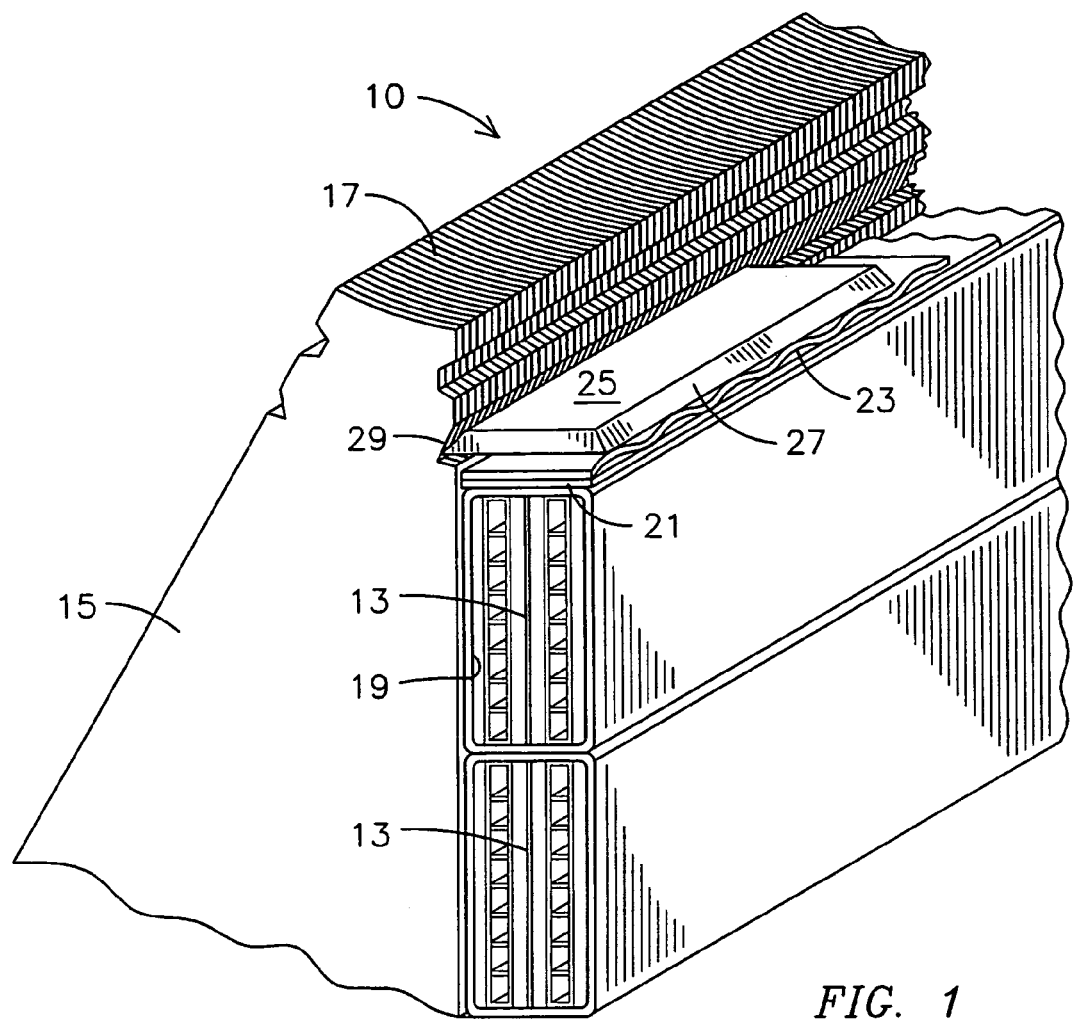
FIG. 1 illustrates a conventional generator stator suitable for use with methods and systems consistent with the present invention.

FIG. 1 illustrates an example of a stator 10 to which methods and systems of the present invention may be applied. The stator 10 includes stator teeth 15; which are formed from multiple, stacked laminations 17. The stator 10 also includes stator slots 19 in which stator coils 13 may be stacked. The stator coils 13 are retained in the slots 19 by shims 21, ripple springs 23, and stator wedges 25 having beveled edges 27 for engaging correspondingly shaped grooves 29 in the sidewalls of the stator teeth 15. The ripple springs 23 are compressed between the stator wedges 25 and shims 21 to generate a force that firmly holds the stator coils 13 in place. Over time, the ripple springs 23 may lose their resiliency so that the stator wedges 25 become loose. This can permit the stator coils 13 to vibrate, which can result in damage to the stator 10 and eventual failure of the electrical generator.

Figure 2:
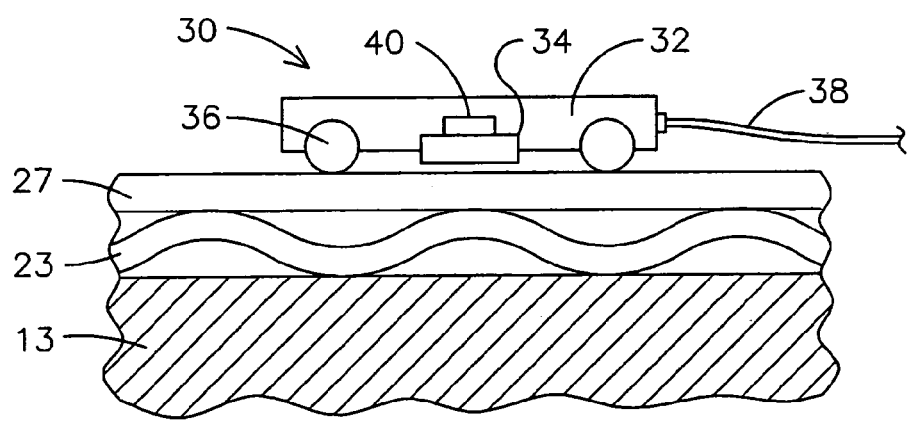
FIG. 2 illustrates an exemplary embodiment of a compression-assessment tool consistent with the present invention.

FIG. 2 illustrates a compression-assessment tool 30 for assessing the tightness of ripple springs that is consistent with an exemplary embodiment of the present invention. The compression-assessment tool 30 is shown resting on a conventional stator wedge 27. A ripple spring 23 is installed between the stator wedge 27 and the stator coil 13. For purposes of explanation, the ripple spring 23 is shown as having the shape of a sign wave. However, the differences between the ripple spring's peaks and crests are actually less pronounced.

Methods and systems consistent with the present invention may be utilized with any stator wedge 25 that is made of a substantially non-conductive material. Most conventional stator wedges 25 are made of a non-conductive material, such as fiberglass. Methods and systems consistent with the present invention may be utilized with any ripple spring 23 that is made of either a substantially non-conductive material or a combination of conductive and non-conductive materials.

The compression-assessment tool 30 illustrated in FIG. 2 includes a carriage 32, which supports a proximity sensor 34. For purposes of methods and systems of the present invention, the proximity sensor 34 may be an inductive or capacitive sensor or any sensor that permits the compression-assessment tool 30 to measure the proximity of the ripple spring 23 through the material of the stator wedge 25. If the ripple spring 25 is non-conductive a capacitive-type sensor is preferred. One example of such a sensor is the capacitive sensor with model number PM475, which is manufactured by Lion Precision, 563 Shoreview Park Road, St. Paul, Minn. 55126. In another embodiment, the ripple spring 25 may include a conductive lining or conductive layer and the proximity sensor may be of the inductive type. The compression assessment tool 30 may also include an amplifier for amplifying output signals from the sensor 34. One example of such an amplifier is the amplifier with model number 99343-04, also available from Lion Precision.

Referring again to the compression-assessment tool 30 illustrated in FIG. 2, the carriage 32 may include wheels 36 or sliding surfaces to facilitate the movement of the compression-assessment tool 30 over the length of the stator wedge 25. The carriage 32 may also include one or more cables 38 for transmitting signals to and from the compression-assessment tool 30. The carriage 32 may also include an adjustment device 40 for adjusting the height and/or position of the proximity sensor 34 relative to the stator wedge 27.

Figure 3:
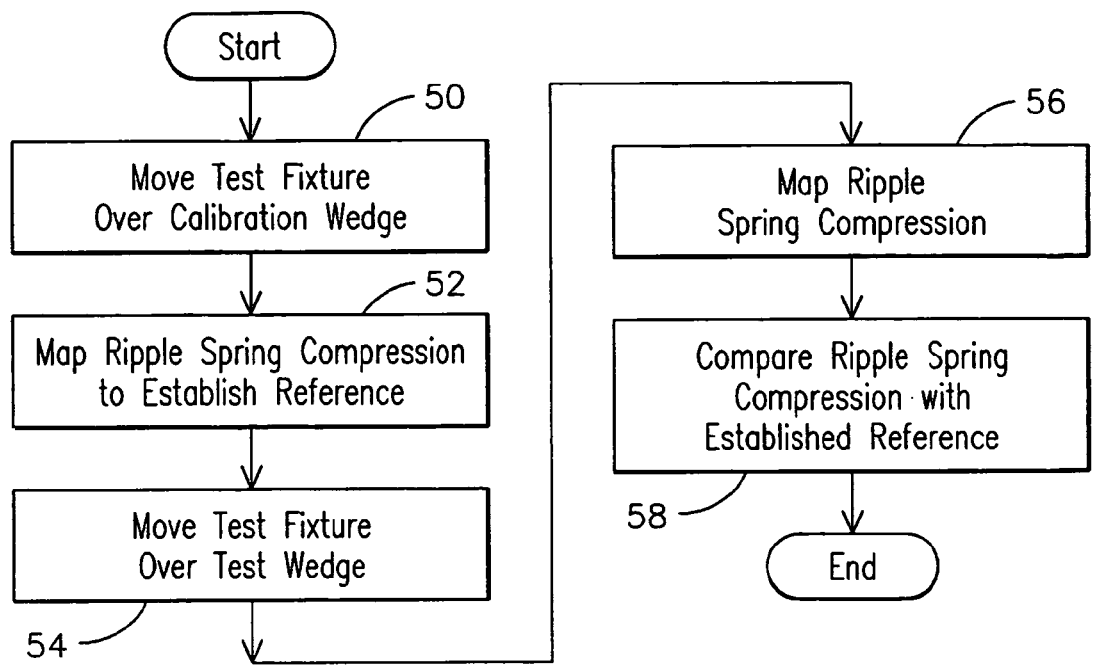
FIG. 3 is a flowchart illustrating steps in an exemplary embodiment of a method consistent with the present invention.

FIG. 3 illustrates exemplary steps for using a compression-assessment tool that is consistent with the present invention. Before assessing the compression of a ripple spring, the compression-assessment tool should be calibrated. The compression-assessment tool may be calibrated, for example, using known information about the size and material of the stator wedge and ripple spring. This may be accomplished, for example, by taking a wedge and ripple spring of the same type as the ones to be tested; putting them into a test fixture; and applying a known force, for example, using a hydraulic press. The compression-assessment tool may then be passed over the text fixture to obtain initial output signals. The compression-assessment tool may then be adjusted to match the output signals to the tightness created by the known force.

Alternatively, the compression-assessment tool may be calibrated using a stator with a ripple spring of known tightness value. The tightness value may come, for example, from one of the conventional compression-assessment methods. With this approach, the compression-assessment tool is next swept over the stator wedge of the reference ripple spring with known tightness (step 50) to produce an output signal that is representative of the tightness of the reference ripple spring. This data may then be used to map the compression of the reference ripple spring over its length (step 52).

Once the reference data has been established, the compression-assessment tool may be swept over the test stator wedge (step 54) to produce an output signal that is representative of the tightness of the test ripple spring. This data is then used to map the compression of the test ripple spring over its length (step 56). The mappings of the reference ripple spring and the test ripple spring may then be compared (step 58) to determine the relative compression of the test ripple spring.

Figure 4:
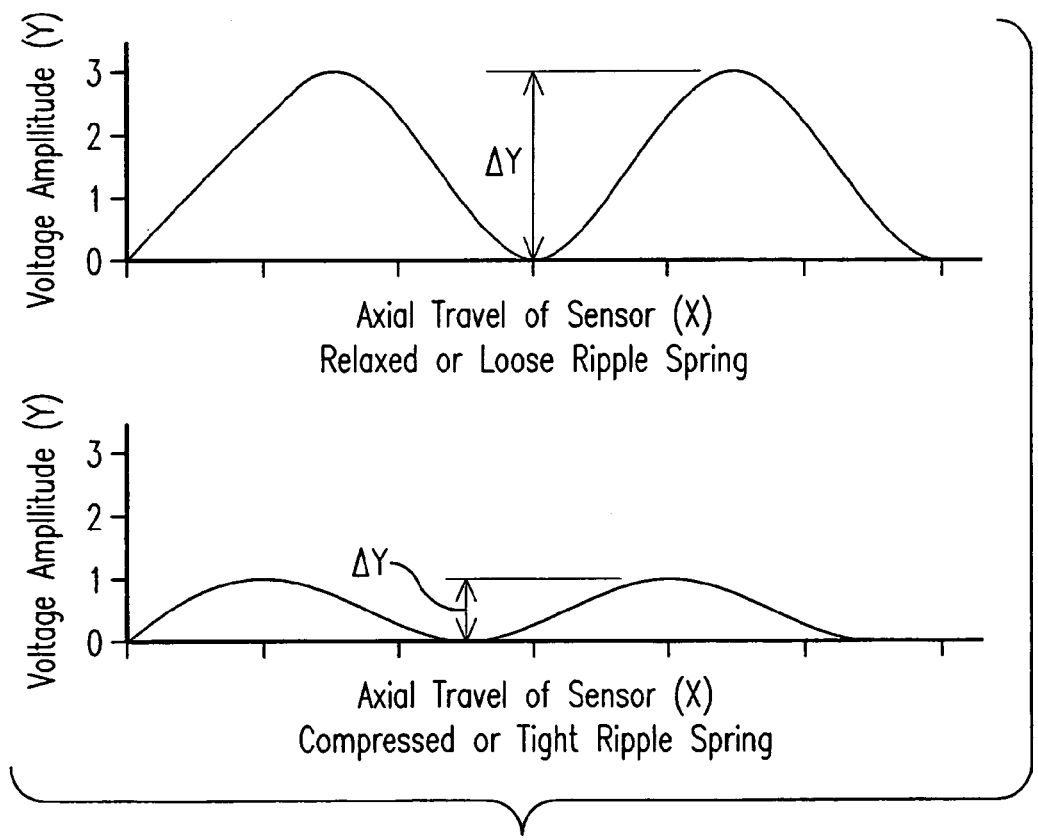
FIG. 4 illustrates exemplary output signals of the compression-assessment tool of FIG. 2.

FIG. 4 illustrates typical output signals for a relaxed and a compressed ripple spring. As the compression-assessment tool is passed axially over a stator wedge, an output signal (represented by Voltage Amplitude (Y) in FIG. 4) is generated by the proximity sensor. This output signal is representative of the tightness or compression of the underlying ripple spring over the Axial Travel of Sensor (X). The output signal may be utilized to create a mapping of the ripple-spring compression over the length of the stator wedge.

Figure 5:
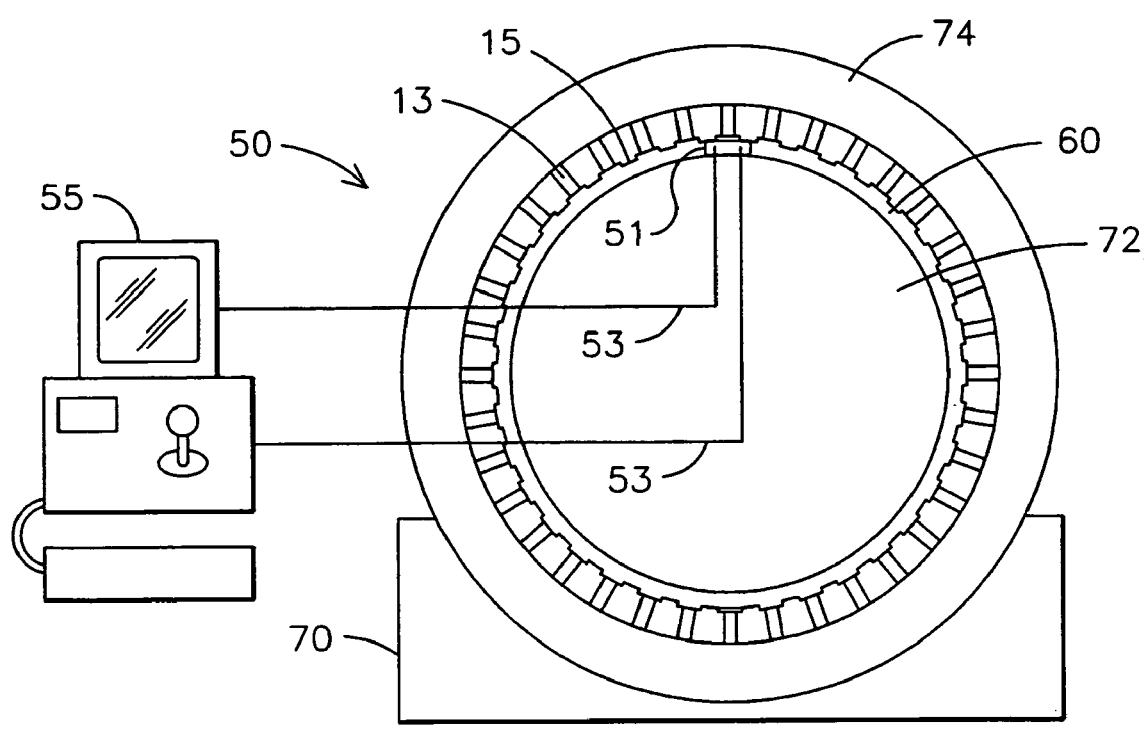
FIG. 5 illustrates a ripple-spring-compression-assessment system consistent with an exemplary embodiment of the present invention.

FIG. 5 illustrates an exemplary embodiment of a compression-assessment system 50 consistent with the present invention. The compression-assessment system 50 includes a low-profile robotic carriage 51 that may be inserted in a narrow gap 60 between the rotor 72 and stator 74 of a dynamoelectric machine 70 such as an electric generator. The robotic carriage 51 may be guided by an operator along the length of a stator slot to inspect the tightness of the wedges in the slot. Electrical signals may be transmitted between the carriage 51 and a data processing system 55 via electrical cables 53 to control positioning of the carriage 51. Output signals from the proximity sensor on the carriage 51 representing the ripple-spring tightness may also be transmitted between the carriage 51 and data processing system 55 over one or more of the electrical cables 53.

The present invention has been described with reference to the accompanying drawings that illustrate preferred embodiments of the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. Thus, the scope of the invention should be determined based upon the appended claims and their legal equivalents, rather than the specific embodiments described above.

What is claimed is:

1. A method of determining the condition of an installed ripple spring in an electric-generator stator with the use of a compression-assessment tool having a non-contact proximity sensor, the method comprising the steps of:
    calibrating the compression-assessment tool;
    placing the compression-assessment tool on the surface of a stator wedge of a test stator having an unknown ripple-spring compression;
    linearly displacing the compression-assessment tool over the length of the stator wedge of the test stator;
    measuring the compression of the ripple spring of the test stator through the stator wedge by directly measuring the proximity of an upper surface of the ripple spring to the compression-assessment tool;
    comparing the output signal obtained from the test stator to a reference output signal obtained from calibrating the compression-assessment tool in order to determine the relative compression and condition of the ripple spring of the test stator.

2. The method of claim 1, wherein the step of calibrating the compression-assessment tool comprises passing the compression-assessment tool over the surface of a stator wedge of a calibration stator having a known ripple-spring compression.

3. The method of claim 1, wherein the step of calibrating the compression-assessment tool comprises placing a calibration wedge and ripple spring into a test fixture, applying a known force to the wedge and ripple spring, passing the compression-assessment tool over the text fixture, measuring output signals from the tool, and adjusting the output signals to correspond to a tightness associated with the known force.

4. The method of claim 1, wherein the step of measuring comprising measuring the compression of the ripple spring with a capacitive-type proximity sensor.

5. The method of claim 1, wherein the step of measuring comprises measuring the compression of the ripple spring with an inductive-type proximity sensor.

6. A system for measuring a compression of a ripple spring installed in a stator of an electric generator, comprising:
- a compression-assessment tool including a carriage for supporting a proximity sensor for measuring the proximity of the ripple spring directly through the stator wedge, the sensor configured for:
- providing a reference output signal representative of a reference distance of the ripple spring from the proximity sensor and representative of at least one of a known compression of the ripple spring and a know force applied to the ripple spring;
- providing a test output signal representative of a test distance of the ripple spring from the proximity sensor and representative of an unknown compression of the ripple spring;
- comparing the test output signal to the reference output signal to determine the relative compression and condition of the ripple spring subject to the unknown compression and
- a carriage for supporting the proximity sensor and for movably passing the sensor substantially linearly over the length of the stator wedge.

7. The system of claim 6, wherein said proximity sensor comprises a capacitive-type proximity sensor.

8. The system of claim 6, wherein said proximity sensor comprises an inductive-type proximity sensor.

9. The system of claim 6, wherein said carriage is a robotic carriage that is movably controllable by an operator.

10. The system of claim 9, further comprising a data processing system for processing and displaying the output signal from the non-contact ripple spring.

11. A system for measuring a compression of a ripple spring installed in a stator of an electric generator, comprising:
- a compression-assessment tool including a carriage for supporting a sensor means for measuring the proximity of the ripple spring directly through the stator wedge, the sensor means configured for:
- providing a reference output signal representative of a reference distance of the ripple spring from the sensor means and representative of a least one of a known compression of the ripple spring and a known force applied to the ripple spring;
- providing a test output signal representative of a test distance of the ripple spring from the proximity sensor and representative of an unknown compression of the ripple spring;
- comparing the test output signal to the reference output signal for determining the relative compression and condition of the ripple spring subject to the unknown compression; and
- a carriage means for supporting the sensor means and for movably passing the sensor substantially linearly over the length of the stator wedge.

12. The system of claim 11, wherein said sensor means comprises a capacitive-type proximity sensor.

13. The system of claim 11, wherein said sensor means comprises an inductive-type proximity sensor.

14. The system of claim 11, wherein said carriage means is a robotic carriage that is movably controllable by an operator.

15. The system of claim 14, further comprising a data processing system for processing and displaying the output signal from the compression-assessment tool.

\* \* \* \* \*